United States Patent [19]

Norsworthy

[11] 4,019,367
[45] Apr. 26, 1977

[54] LINEARIZED ODOR TRANSDUCER
[75] Inventor: Ross W. Norsworthy, Largo, Fla.
[73] Assignee: CRS Industries, Inc., Tampa, Fla.
[22] Filed: Sept. 11, 1975
[21] Appl. No.: 612,458
[52] U.S. Cl. .................................................. 73/23
[51] Int. Cl.² ...................................... G01N 27/04
[58] Field of Search ...................... 73/23, 27 R, 25; 23/232 E, 254 E; 324/65 R, 71 SN; 340/237 R

[56] References Cited
UNITED STATES PATENTS

| | | | |
|---|---|---|---|
| 3,562,521 | 2/1971 | Vanderschmidt | 73/23 |
| 3,695,848 | 10/1972 | Taguchi | 73/27 R |
| 3,864,628 | 2/1975 | Klass et al. | 73/23 |
| 3,886,785 | 6/1975 | Stadler et al. | 73/27 R |

Primary Examiner—Richard C. Queisser
Assistant Examiner—Stephen A. Kreitman
Attorney, Agent, or Firm—Stefan M. Stein; Robert F. Frijouf

[57] ABSTRACT

This invention relates to an improved method and apparatus for the detection and measurement of concentrations of foreign substances in a fluid, particularly atmospheric gas. Transducers and signal modifying devices are electronically connected in a predetermined arrangement so as to determine the concentration of foreign matter and display this concentration as a linear function determined by the amount of foreign matter found.

6 Claims, 1 Drawing Figure

LINEARIZED ODOR TRANSDUCER

BACKGROUND OF THE INVENTION

1. Field of the Invention

An odor transducer for the detection and measurement of foreign matter contained in a fluid substance, particularly atmosphere.

2. Description of the Prior Art

In recent years there has been a rapid increase in the knowledge concerning the deleterious effects of air pollution upon animal life. Sophisticated systems for the removal of pollutants from the atmosphere have been developed. Such systems include prior art devices and systems for measuring the amounts of such pollutants.

Generally speaking, air pollution is largely made up of small particulate matter. These particles are usually in the submicron range and are suspended in the fluid atmosphere. In order to operate many of the pollution removal systems at or near maximum efficiency, it is necessary to know the concentration of pollutants in the atmosphere. Prior art methods of measuring the pollutant concentration have typically used sensing elements or transducers whose resistance varies in some proportion to the pollutants present. Usually, the transducer is one arm of a bridge. This method of measuring pollutants is complex in that the bridge circuit requires continual balancing by trained personnel.

Other pollutant measuring devices use operational amplifiers in a feedback configuration. This has the advantage of being relatively easy to operate. However, the output of these devices is a non-linear function of the concentration. The non-linear display of concentration is awkward and difficult to work with in a pollution detector system.

In operation, it is well recognized that, the signal from the detection system can be used to control the pollution abatement device. In this application, a non-linear signal causes problems in controlling the abatement system. Also, if the output is merely to be displayed or recorded, a non-linear signal requires scale changes and constant monitoring to assure a readable scale is being used.

It is desirable to have the concentration of pollutants displayed as a linear function by a relatively simple, inexpensive and easy to operate sensing device.

SUMMARY OF THE INVENTION

This invention involves a method and device of measuring the concentration of particulate matter in a fluid. More particularly, the invention is designed to determine the concentration of pollutant particles in the atmosphere and to output or display the particulate concentration as a linear function.

The desired goal of the subject invention is to detect odor causing or like pollutants in the atmosphere and measure their concentration. This is achieved through the use of transducers, the resistance of which varies in proportion to the square root of the concentration of the odor or pollution to be detected. Typically, $$R_s = A_o C^{-1/2}$$

can be written as:

$$R_s = (1/\sqrt{A_o C}) \quad \text{(Eq. 1)}$$

where $R_s$ is the resistance in ohms of the semiconductor transducer, $C$ is the odor concentration in parts per million (ppm), and $A_o$ is a constant in ohms. It is desired to obtain a linear output, i.e., the signal should be directly proportional to the concentration. The equation for the output should be of the form:

$$V_o = K_o C \quad \text{(Eq. 2)}$$

where $K_o$ is a constant for a particular pollutant or odor, and $C$ is the concentration.

To obtain an output in the form of Equation 2, two transducers are used with two signal modifying devices. Typically, the signal modifying devices are operational amplifiers. The linear output is obtained in the following manner. The transfer function for a negative feedback inverting operational amplifier is:

$$V_{o1} = -V_{in}(R_f/R_s) \quad \text{(Eq. 3)}$$

where $V_{o1}$ is the output voltage, $V_{in}$ is the input voltage, $R_f$ is the feedback resistance and $R_s$ is the input resistance of the operational amplifier. Now, by connecting two such operational amplifiers in series, the output is:

$$V_{o2} = V_{o1}(R_f/R_s) = V_{in}(R_f^2/R_s^2)$$

However, $R_s$ is the resistance of the semiconductor transducer (Eq. 1), thus:

$$V_{o2} = V_{in}(R_f^2/A_o^2) C$$

of $$V_{o2} = K_o C \quad \text{(Eq. 4)}$$

The output voltage of the odor detector is now in the desired linear form where $K_o$ is a constant which can be varied to provide the desired range of output voltage.

The odor sensor or detector comprises power supplies for the transducers, signal modifying devices and a reference voltage supply. The transducers are positioned so as to be exposed to the atmosphere, the odor, or pollutant concentration causing this odor, of which is to be determined. The transducers are electrically connected to the inputs of the signal modifying devices. The reference voltage, or $V_{in}$, is input to the first transducer and the output of the first transducer and signal modifying device is input to the second transducer. The output of the second signal modifying device is expressed by Equation 4 (4) above.

The invention accordingly comprises the features of construction, combination of elements and arrangement of parts which will be exemplified in the construction hereinafter set forth and the scope of the invention will be indicated in the claims.

BRIEF DESCRIPTION OF THE DRAWINGS

For a fuller understanding of the nature and objects of the invention, reference should be had to the following detailed description, taken in connection with the accompanying drawings in which.

Similar reference characters refer to similar parts throughout the several views of the drawings.

DETAILED DESCRIPTION OF THE PREFERRED EMBODIMENT

Figure 1:
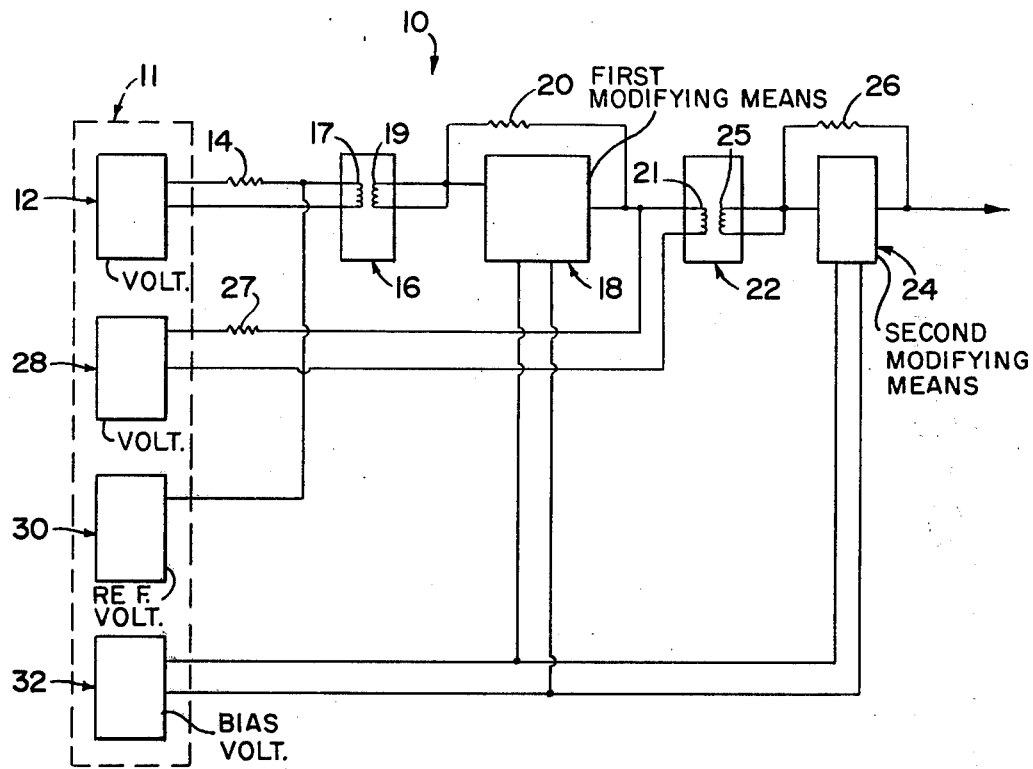
FIG. 1 is a block diagram of the linear odor sensor invention.

The linear odor sensor means is generally indicated as 10 in FIG. 1, a block diagram of the invention. While the terminology of the present invention is described with general reference to an odor sensor, it should be clear that the subject invention is capable of detection and display of various type pollutants which may be present in the atmosphere. Linear odor sensor means 10 comprises power supply means 11 which provides electrical power to the invention. Power supply means 11 are electrically connected to first and second transducer means 16 and 22, first and second signal modifying means 18 and 24, and first and second resistor means 14 and 27 as will be further detailed hereinafter.

Power supply means 11 further comprises first and second voltage supply means 12 and 28, respectively, reference voltage supply means 30 and bias voltage supply means 32. First resistor means 14 is in electrical communication with one side of first voltage supply means 12. First transducer means 16 is electrically connected to first resistor means 14 and to the other side of first voltage supply means 12 completing the circuit.

First and second transducer means 16 and 22 may comprise Figaro Engineering, Inc., T.G.S. No. 109 transducers in the preferred embodiment. However, it is anticipated that any suitable transducer can be used in the linear odor sensor means 10. The first and second transducer means 16 and 22 each have four leads, two for the heater element and two for the particulate detection element. As described above, first voltage supply means 12 is in electrical connection with the heater 17 of first transducer means 16 through first resistor means 14.

One side of the detector element 19 of first transducer means 16 is electrically input to first signal modifying means 18. The other side of the detector element 19 of first transducer means 16 is electrically connected to the output of first signal modifying means 18. First feedback resistor means 20 is in electrical communication between the input and the output of first signal modifying means 18. The output of first signal modifying means 18 is in electrical contact with one side of the heater 21 of second transducer means 22. Also in electrical contact with this same side of heater 21 is the second voltage supply means 28 through second resistor means 27. The other side of the output of second voltage supply means 28 is connected to the other side of the heater 21 of the second transducer means 22. side of the detector element 25 of the second transducer means 22 is electrically connected to the input of the second signal modifying means 24. The other side of the detector element 25 of the second transducer means 22 is electrically connected to the second signal modifying means 24. Second feedback resistor means 26 is in electrical communication between the input and the output of second signal modifying means 24. Output from second signal modifying means 24 is the signal which is directly proportional to the concentration of pollutant in the atmosphere surrounding first and second transducer means 16 and 22.

Reference voltage supply means 30 is in electrical connection with one side of the heater 17 of first transducer means 16.

In the preferred embodiment reference voltage supply means 30 may comprise a Motorola MC1723CL voltage regulator. It is contemplated that any appropriate means of supplying a reference voltage for first transducer means 16 will suffice.

Bias volume supply means 32 outputs a DC voltage and is electrically connected to both first and second signal modifying means 18 and 24. This bias voltage supply means 32 further is in electrical supplying communication with the reference voltage supply means 30.

In the preferred embodiment power supply means 11 is connected to a standard 120 volt, 60 hertz electrical source. First and second voltage supply means 12 and 28 are the 6.3 volt center tap from a filament transformer. Bias supply means 32 comprises a 12.6 volt center tap filament transformer with 1N5552 diodes, or equivalent, in electrical connection with the outputs. The B+ and B− from bias supply means 32 operate to bias first and second signal modifying means 18 and 24 and reference voltage supply means 30. It is to be recognized that there are many ways in which power supply means 11 may be configured. The preferred embodiment is only one of these ways and any method of supplying the required power to first and second transducer means 16 and 22 and first and second signal modifying means 18 and 24 is within the scope of the invention.

First and second signal modifying means 18 and 24 comprise MC1741CP1 Motorola operational amplifiers in the preferred embodiment. It is within the contemplation of the invention that any signal modifying means, such as digital filters or the like, can be used to achieve the linear output signal.

In operation, the linear odor sensor means is positioned so that first and second transducer means 16 and 22 are within the atmosphere, of which, the odor or other type pollutant concentration is to be determined. Power supply means 11 is engaged to provide electrical power in the circuit. The heaters 17 and 21 of first and second transducer means 16 and 22 respectively, are activated and the detector elements 19 and 25 of said first and second transducer means 16 and 22 respectively, pick up the current created by the ionized particulate matter. A voltage is thereby generated dependent upon the concentration of the odor or pollutant. First and second signal modifying means 18 and 24, operating linearly, amplify the signal output from first and second transducer means 16 and 22, respectively. As explained above, the signal output from second signal modifying means 24 is a linear function of the concentration.

It will thus be seen that the objects set forth above, among those made apparent from the preceding description, are efficiently attained, and since certain changes may be made in carrying out the above method and article without departing from the scope of the invention, it is intended that all matter contained in the above description shall be interpreted as illustrative and not in a limiting sense.

It is also to be understood that the following claims are intended to cover all the generic and specific features of the invention herein described, and all statements of the scope of the invention, which, as a matter of language, might be said to fall therebetween.

Now that the invention has been described,

What is claimed is:

1. A pollutant sensing means for indicating the amount of pollutants in a gas, comprising the combination:

a first and second pollutant transducer means each providing a change in resistance as a function of the concentration of pollutant present in the gas;

a first and a second signal modifying means, electrical power source means connected to said first and second pollutant transducer means and to said first and second signal modifying means;

reference power source means, first means connecting said first pollutant transducer means to said reference power source means and connecting the output signal of said first pollutant transducer means to said first signal modifying means for providing a first outout signal in accordance with the change in resistance of said first pollutant transducer means relative to said reference power source means; and second means connecting said second pollutant transducer means to said first output signal of said first signal modifying means and connecting the output of said second pollutant transducer means to said second signal modifying means for providing a second output signal in accordance with the change in resistance of said second pollutant transducer means relative to said first output signal.

2. A pollutant sensing means as set forth in claim 1, wherein said first means includes means connecting said second signal modifying means for providing a substantially linear output signal as a function of concentration of pollutant present in the gas.

3. A pollutant sensing means as set forth in claim 1, wherein said first pollutant transducer means include first heater means and first detector means; and said first means includes means connecting said reference power source means to said first heater means and means connecting said first detector means to the input of said first signal modifying means.

4. A pollutant sensing means as set forth in claim 3, wherein said second pollutant transducer means includes second heater means and second detector means; and said second means include means connecting said first output signal of said first signal modifying means to said second heater means and means connecting said second detector means to the input of said second signal modifying means.

5. A pollutant sensing means as set forth in claim 1, wherein each of said first and second signal modifying means include amplifier means.

6. A pollutant sensing means comprising first and second transducer means, wherein said first and second transducer means further comprise first and second heater means and first and second detector means respectively; first resistor means in electrical communication with said first heater means; first voltage supply means in electrical communication with said first resistor means and with said first heater means; reference voltage supply means in electrical connection with said first heater means, first operational amplifier means in electrical communication with said first detector means, first feedback resistor means in electrical contact with said first detector means and with the output of said first operational amplifier means, second resistor means in electrical contact with said second heater means of said second transducer means, second voltage supply means in electrical contact with said second resistor means and with said second heater means, the output of said first operational amplifier in electrical communication with said second heater means, second operational amplifier means in electrical communication with said second detector means, second feedback resistor means in electrical contact with said second detector means, and in electrical contact with the output of said second operational amplifier means, bias voltage supply in electrical supplying relationship with said first and second operational amplifier means.

* * * * *